US011548925B2

(12) United States Patent
Li et al.

(10) Patent No.: US 11,548,925 B2
(45) Date of Patent: Jan. 10, 2023

(54) CACNA1H-DERIVED TUMOR ANTIGEN POLYPEPTIDE AND USE THEREOF

(71) Applicant: Genoimmune Therapeutics Co., Ltd., Hubei (CN)

(72) Inventors: Guanglei Li, Guangdong (CN); Yong Hou, Guangdong (CN); Shuntao Luo, Guangdong (CN); Xiumei Lin, Guangdong (CN); Ting An, Guangdong (CN); Bo Li, Guangdong (CN); Wei Zhang, Guangdong (CN); Chengchi Chao, Guangdong (CN); Zhen Cheng, Guangdong (CN); Handong Li, Guangdong (CN); Naibo Yang, Guangdong (CN)

(73) Assignee: GENOIMMUNE THERAPEUTICS CO., LTD., Wuhan (CN)

( * ) Notice: Subject to any disclaimer, the term of this patent is extended or adjusted under 35 U.S.C. 154(b) by 125 days.

(21) Appl. No.: 16/338,126

(22) PCT Filed: Sep. 30, 2016

(86) PCT No.: PCT/CN2016/100978
§ 371 (c)(1),
(2) Date: Mar. 29, 2019

(87) PCT Pub. No.: WO2018/058489
PCT Pub. Date: Apr. 5, 2018

(65) Prior Publication Data

US 2020/0024316 A1 Jan. 23, 2020

(51) Int. Cl.

| | |
|---|---|
| ***C07K 14/47*** | (2006.01) |
| ***A61P 35/00*** | (2006.01) |
| ***G01N 33/574*** | (2006.01) |
| ***A61K 39/00*** | (2006.01) |
| ***C07K 14/705*** | (2006.01) |

(52) U.S. Cl.
CPC .. *C07K 14/4748* (2013.01); *A61K 39/001102* (2018.08); *A61P 35/00* (2018.01); *C07K 14/705* (2013.01); *G01N 33/57492* (2013.01); *A61K 2039/572* (2013.01)

(58) Field of Classification Search
CPC ... C07K 14/4748; C07K 14/705; A61P 35/00; A61K 39/001102; A61K 2039/572; G01N 33/57492
See application file for complete search history.

(56) References Cited

FOREIGN PATENT DOCUMENTS

| | | | |
|---|---|---|---|
| CN | 1521268 | A | 8/2004 |
| CN | 102659921 | A | 9/2012 |
| CN | 103570818 | A | 2/2014 |
| CN | 103957923 | A | 7/2014 |
| CN | 104830779 | A | 8/2015 |

OTHER PUBLICATIONS

Jones, Pharmacogenomics Journal (2001) 1:126-134. (Year: 2001).*
Tosatto et al., Current Pharmaceutical Design (2006), 12:2067-2086. (Year: 2006).*
Int'l Search Report dated Jun. 7, 2017 in Int'l Application No. PCT/CN2016/100978.
Office Action dated Nov. 16, 2021 in Chinese Application No. 201680089572.9.
Meng et al., "In vitro immune response of cytotoxic T lymphocyte induced by dendritic cells pulsed with tumor associated antigen MUC4", ACTA Universitatis Medicinalis Nanjing (Natural Science), vol. 27, No. 12, pp. 1353-1357 and 1 page of supplemental data (2007). (Includes English Abstract).
Office Action dated Jul. 5, 2022 in Chinese Application No. 201680089572.9.
Ren et al., "Identification of an HLA-A2 restricted HBcAg-specific T cell epitope derived from HBV genotypes B and C", Science China Press, vol. 55, No. 30, pp. 2915-2924 and 2 pages of supplemental data (2010). (Includes English Abstract).

* cited by examiner

*Primary Examiner* — Jessica H Roark
*Assistant Examiner* — Cheom-Gil Cheong
(74) *Attorney, Agent, or Firm* — Panitch Schwarze Belisario & Nadel LLP; Stephany G. Small; Lars H. Genieser

(57) ABSTRACT

Provided are a tumor antigen polypeptide having the amino acid sequence as shown in SEQ ID NO: 2 or a variant thereof; a nucleic acid encoding the same; a nucleic acid construct, an expression vector, and a host cell containing the encoding nucleic acid; and an antigen presenting cell presenting the tumor antigen polypeptide on the cell surface and an immune effector cell thereof. Also provided is the use of the polypeptide, nucleic acid, antigen presenting cell or immune effector cell in the diagnosis, prevention and treatment of cancers.

9 Claims, 6 Drawing Sheets

Specification includes a Sequence Listing.

CACNA1H-DERIVED TUMOR ANTIGEN POLYPEPTIDE AND USE THEREOF

CROSS-REFERENCE TO RELATED APPLICATION

This application is a Section 371 of International Application No. PCT/CN2016/100978, filed Sep. 30, 2016, which was published in the Chinese language on Apr. 5, 2018, under International Publication No. WO 2018/058489 A1, the disclosure of which is incorporated herein by reference in its entirety.

REFERENCE TO SEQUENCE LISTING SUBMITTED ELECTRONICALLY

This application contains a sequence listing, which is submitted electronically via EFS-Web as an ASCII formatted sequence listing with a file name "Sequence Listing 688287 7US", creation date of Aug. 13, 2021, and having a size of 3.88 KB. The sequence listing submitted via EFS-Web is part of the specification and is herein incorporated by reference in its entirety.

TECHNICAL FIELD

The present invention relates to the technical field of the diagnosis, prevention and immunotherapy of cancers, and in particular to a tumor antigen peptide resulting from mutation of CACNA1H gene, the related products thereof, and the medical use thereof.

BACKGROUND

Cancer is a disease in which cell proliferation is out of control due to genetic mutations in cells. At present, it has become a major threat to human health and is one of the main causes of human death. According to the "Global Cancer Report 2014" published by World Health Organization (WHO), cancer patients and death cases were rapidly increased in 2012 worldwide with nearly half of new cancer cases occurred in Asia, most of which occurred in China, and the amount of new cancer cases in China ranks the first in the world[1]. According to data from "Annual Report of Cancer Registration in China in 2012", about 3.5 million new cancer cases every year were reported in China, and about 2.5 million people died therefrom[2]. Therefore, it would be of great clinical value to find a highly effective and specific cancer treatment method.

Traditional treatments for tumor mainly include surgery, radiotherapy and chemotherapy. However, these therapies have serious limitations. For example, the tumor metastasis and recurrence rate after surgical resection is high due to proximal invasion or distant metastasis of cancer cells, and radiotherapy and chemotherapy can cause serious damage to the body's own normal cells, especially hematopoietic system and immune system of the body, and it is therefore difficult for patients who have developed tumor metastasis to achieve better long-term efficacy[3]. With in-depth studies of the molecular mechanism of tumors and further development of biotechnology, targeted drug therapies and immunotherapies play an increasingly important role in the comprehensive treatment of tumors. The targeted therapies mainly include monoclonal antibodies (sometimes classified as passive immunotherapy) and small molecule targeted drugs, and the immunotherapies mainly include cytokine therapy, immune checkpoint monoclonal antibody, adoptive cell transfer and tumor vaccine, etc.[4, 5]. Immunotherapies control and kill tumor cells by activating the immune system of the body and enhancing the anti-tumor immunity of tumor microenvironment, and thus have the advantages of high efficiency and specificity and good tolerance, and have broad prospects in cancer treatment[5, 6].

Vaccines for tumor immunotherapy mainly include tumor cell vaccines, dendritic cell vaccines, protein & peptide vaccines, nucleic acid vaccines, genetic engineering vaccines and anti-idiotype tumor vaccines[7]. The main mechanism of these vaccines in killing a tumor is the initiation of an immune response against tumor-specific antigen in a patient, including antigen-antibody reaction and a CTL-specific killing and the like, among which the CTL-specific killing plays a great role in immune responses to tumors. A tumor-specific peptide is a tumor-specific antigen that primarily causes CTL-specific killing, and includes tumor-specific mutant peptides as well as tumor-specific highly expressed peptides. Wherein, the tumor-specific mutant peptides are only present in tumor tissues of patients and therefore can act as a specific target of tumor immunotherapy, which has the characteristics of good safety and few side effects. Immunotherapies targeting tumor-specific mutant peptides, such as peptide-specific DC-CTL and TIL adoptive transfer, have a good therapeutic effect[8, 9].

Tumor-specific peptides can be recognized by CTL or TIL cells by virtue of the antigen presenting function of human leukocyte antigen (HLA). The human leukocyte antigen is mainly divided into two subtypes I and II. Type I HLA is further mainly divided into three subtypes A, B and C, each of which can be further divided into multiple subtypes depending on its sequence. HLA-A0201 is one of the HLA-A subtypes, and occurs in 13% of the Chinese population, which is a high proportion. Different peptides bind to the HLA-A0201 subtype with different binding affinities. In a tumor patient with a specific HLA subtype, due to the specific HLA subtype, only a portion of mutant peptides can bind to the HLA and be presented to CTL or TIL cells by the HLA.

The CACNA1H gene encodes a protein having a length of 2353 amino acids and a molecular weight of 259,163 daltons, which acts as a subunit of T-type calcium channel Cav3.2, a voltage-sensitive calcium channel, and is involved in the transport of calcium ions into excitable cells and involved in multiple calcium-dependent processes including muscle contraction, release of hormones or neurotransmitters, gene expression, cell movement, division and death, etc.

REFERENCES

[1] World Health Organization. Globocan 2012: Estimated cancer incidence, mortality and prevalence worldwide in 2012.

[2] Bernard W. Stewart C P W. World Cancer Report 2014. 2014.

[3] Xiaoqin Ha, Shangdi Zhang, Zhihua Yang, Jun Zhang. A new technology for tumor biotherapy—targeted gene therapy. Medicine Journal of Chinese People's Liberation Army 2014; 26:24-7.

[4] Mellman I, Coukos G, Dranoff G. Cancer immunotherapy comes of age. Nature 2011; 480:480-9.

[5] Chen D S, Mellman I. Oncology meets immunology: the cancer-immunity cycle. Immunity 2013; 39:1-10.

[6] Currie G A. Eighty years of immunotherapy: a review of immunological methods used for the treatment of human cancer. British journal of cancer 1972; 26:141-53.

[7] Tingting Li, Hui Li, Xicai Wang. The progress of tumor vaccine in oncotherapy. Journal of Modern Oncology 2013; 21:2351-3

[8] Tran E, Turcotte S, Gros A, et al. Cancer immunotherapy based on mutation-specific CD4+ T cells in a patient with epithelial cancer. Science. 2014. 344(6184): 641-5.

[9] Cobbold M, De La Pena H, Norris A, et al. MHC class I-associated phosphopeptides are the targets of memory-like immunity in leukemia. Sci Transl Med. 2013. 5(203): 203ra125.

SUMMARY OF THE INVENTION

The object of the present invention is to provide a tumor antigen peptide resulting from mutation of the CACNA1H gene, a nucleic acid encoding the tumor antigen peptide, a nucleic acid construct, an expression vector and a host cell comprising the nucleic acid, and an antigen-presenting cell and an immune effector cell of the tumor antigen peptide, and the medical use thereof.

Mutation of the CACNA1H gene causes a change in its amino acid sequence such that the amino acid at position 1428 is mutated from arginine to methionine. The mutated CACNA1H gene is expressed at a high level in tumor tissues and, therefore, enables high expression of the related peptide in tumor tissues. So far, the tumor-specific peptide sequence caused by the above mutation of CACNA1H gene has not been reported in China and abroad, nor has the peptide been used in immunotherapy of tumors. Since the peptide is expressed only in mutated tumor tissues, it is specific for tumor tissues, thus having important significance for the detection, early prevention and immunotherapy of tumors in patients.

In a first aspect, the present invention provides an isolated peptide selected from the group consisting of:

(a) a peptide consisting of the amino acid sequence shown in SEQ ID NO: 2;

(b) a peptide which is derived from the amino acid sequence shown in SEQ ID NO: 2 by substitution, addition and/or deletion of one or more amino acid residues therein, and has the ability to induce cytotoxic T lymphocytes; and (c) a variant or derivative of the peptide (a) or (b) that has the ability to induce cytotoxic T lymphocytes, or an immunologically active fragment thereof.

The inventors of the present invention have found from the melanoma database that mutation of the CACNA1H gene results in the mutation of the encoded amino acid at position 1428 from arginine (Arg, R) to methionine (Met, M), and have predicted by a computer prediction software that the mutant peptide sequence has a high affinity to HLA-A, especially to HLA-A0201. The peptide consists of 9 amino acids with a molecular weight of 974.23 Daltons and a full length sequence of: TLISSLMPI (i.e., SEQ ID NO: 2). By chemically synthesizing the peptide and then subjecting the same to an affinity test to T2 cells, it has been confirmed that the peptide does have a high affinity to HLA-A, especially to HLA-A0201. It has been confirmed by in vitro immunogenicity assay (ELISPOT) that the peptide could induce antigen-specific T cells to secrete the cytokine IFN-γ, and induce an activation reaction of immune cells; and it has been confirmed by LDH-releasing assay that CD8+ T cells could specifically recognize and kill target cells presenting the peptide.

The inventors have also found that the peptide (b) which is derived from the amino acid sequence of the peptide (a) by substitution, addition or deletion of one or more amino acid residues therein may have the above-described functions of the peptide (a), i.e., having a high affinity to HLA-A, especially to HLA-A0201, and able to be specifically recognized by CD8+ T cells, thereby causing a specific immune response; and having an ability to induce cytotoxic T lymphocyte.

Preferably, the substitution, addition and/or deletion of one or more amino acids is the substitution of the amino acid at position 2 and/or position 9 of the amino acid sequence as shown in SEQ ID NO: 2.

More preferably, the substitution, addition and/or deletion of one or more amino acids is the substitution of M for the amino acid at position 2 and/or of L or V for the amino acid at position 9 of the amino acid sequence as shown in SEQ ID NO: 2.

More preferably, the peptide (b) has the amino acid sequence as shown in SEQ ID NO: 3 (i.e., TLISSLMPL), SEQ ID NO: 4 (i.e., TLISSLMPV), SEQ ID NO: 5 (i.e., TMISSLMPI), SEQ ID NO: 6 (i.e., TMISSLMPL), or SEQ ID NO: 7 (i.e., TMISSLMPV).

It has been experimentally verified that, compared to the peptide (a), the peptide (b)'s binding affinity to HLA-A, especially to HLA-A0201, is enhanced, but its specificity for T cells is not changed. Thus, both the peptide (b) and the peptide (a) have the same ability to activate a specific T immune.

The peptides of the present invention can be synthesized according to methods used in conventional peptide chemistry, including, for example, the methods described in Peptide Synthesis, Interscience, New York, 1966; and the peptides of the present invention can also be prepared by conventional genetic engineering. For example, conventional DNA synthesis and genetic engineering methods can be used to prepare the peptide by preparing a nucleotide encoding the same, for example by the following procedure: inserting the nucleotide described above into a commonly used expression vector; transforming a host cell with the resulting recombinant expression vector; culturing the resulting transformant; and collecting the peptide from the culture, all of which can be carried out, for example, by referring to the method described in Molecular Cloning, T. Maniatis et al., CSH Laboratory (1983). The peptide obtained by the above method can be verified by reversed-phase high-performance liquid chromatography-mass spectrometry.

In a second aspect, the present invention provides an isolated nucleic acid encoding the isolated peptide as described in the first aspect.

In a third aspect, the present invention provides a nucleic acid construct comprising the nucleic acid as described in the second aspect, and one or more control sequences operably linked thereto and able to direct the production of the peptide in an expression host.

In a fourth aspect, the present invention provides an expression vector comprising the nucleic acid construct as described in the third aspect.

In a fifth aspect, the present invention provides a host cell into which the nucleic acid construct as described in the third aspect or the expression vector as described in the fourth aspect has been transformed or transfected.

In a sixth aspect, the present invention provides an antigen-presenting cell which presents the isolated peptide as described in the first aspect on the cell surface.

In a seventh aspect, the present invention provides a method for producing the antigen-presenting cell as described in the sixth aspect, comprising the step of: contacting the peptide as described in the first aspect with a cell having an antigen-presenting ability, or comprising the steps of: introducing the nucleic acid as described in the second aspect, or the nucleic acid construct as described in the third aspect, or the expression vector as described in the fourth aspect into a cell having an antigen-presenting ability and expressing the same therein.

Preferably, the cell having an antigen-presenting ability is a dendritic cell.

In an eighth aspect, the present invention provides an immune effector cell which can recognize the peptide as described in the first aspect, or recognize an antigen-presenting cell which presents the peptide as described in the first aspect on the cell surface.

In a ninth aspect, the present invention provides a method for producing the immune effector cell as described in the eighth aspect, comprising the step of: contacting the antigen-presenting cell as described in the sixth aspect with a cell with the ability of immune effect.

Preferably, the cell with the ability of immune effect is a T cell, preferably a CD8+ T cell.

In a tenth aspect, the present invention provides a targeted immune cell population which is formed by mixing and co-cultivating antigen-presenting cells with lymphocytes.

In an eleventh aspect, the present invention provides a conjugate comprising the peptide as described in the first aspect and an anti-cancer drug.

In a twelfth aspect, the present invention provides an antibody which can specifically recognize the peptide as described in the first aspect.

In a thirteenth aspect, the present invention provides a method for producing an antibody, comprising:

immunizing an animal with the peptide as described in the first aspect;

collecting serum of the immunized animal; and purifying the antibody of interest from the serum.

In a fourteenth aspect, the present invention provides a vaccine for treating or preventing a cancer in a patient, comprising the peptide as described in the first aspect, or the nucleic acid as described in the second aspect, or the nucleic acid construct as described in the third aspect, or the expression vector as described in the fourth aspect, or the antigen-presenting cell as described in the sixth aspect, or the immune effector cell as described in the eighth aspect.

Preferably, the cancer is a cancer in which the peptide as described in the first aspect is expressed.

More preferably, the cancer is selected from the group consisting of lung cancer, melanoma, breast cancer, nasopharyngeal carcinoma, liver cancer, gastric cancer, esophageal cancer, colorectal cancer, pancreatic cancer, skin cancer, prostate cancer, cervical cancer, leukemia, and brain tumors.

In a fifteenth aspect, the present invention provides a pharmaceutical composition for treating or preventing a cancer in a patient, comprising the peptide as described in the first aspect, and a pharmaceutically acceptable carrier.

In a sixteenth aspect, the present invention provides use of the peptide as described in the first aspect for the preparation of an antibody for preventing or treating a tumor.

Optionally, the tumor expresses both HLA-A0201 and the peptide.

Optionally, the tumor is selected from lung cancer, melanoma, breast cancer, nasopharyngeal carcinoma, liver cancer, gastric cancer, esophageal cancer, colorectal cancer, pancreatic cancer, skin cancer, prostate cancer, cervical cancer, leukemia, and brain tumors.

In a seventeenth aspect, the present invention provides use of the peptide as described in the first aspect for the preparation of a medicament for preventing or treating a tumor.

Optionally, the tumor expresses both HLA-A0201 and the peptide.

Optionally, the tumor is selected from lung cancer, melanoma, breast cancer, nasopharyngeal carcinoma, liver cancer, gastric cancer, esophageal cancer, colorectal cancer, pancreatic cancer, skin cancer, prostate cancer, cervical cancer, leukemia, and brain tumors.

In an eighteenth aspect, the present invention provides use of the peptide as described in the first aspect for the preparation of a vaccine for preventing or treating a tumor.

Optionally, the tumor expresses both HLA-A0201 and the peptide.

Optionally, the tumor is selected from lung cancer, melanoma, breast cancer, nasopharyngeal carcinoma, liver cancer, gastric cancer, esophageal cancer, colorectal cancer, pancreatic cancer, skin cancer, prostate cancer, cervical cancer, leukemia, and brain tumors.

In a nineteenth aspect, the present invention provides use of a detection reagent for the peptide as described in the first aspect or for the nucleic acid as described in the second aspect for the preparation of a kit for diagnosing a cancer in a patient.

Preferably, the cancer is a cancer in which the peptide as described in the first aspect is expressed.

More preferably, the cancer is selected from the group consisting of lung cancer, melanoma, breast cancer, nasopharyngeal carcinoma, liver cancer, gastric cancer, esophageal cancer, colorectal cancer, pancreatic cancer, skin cancer, prostate cancer, cervical cancer, leukemia, and brain tumors.

In a twentieth aspect, the present invention provides a kit for diagnosing a cancer in a patient, comprising a detection reagent for the peptide as described in the first aspect or for the nucleic acid as described in the second aspect.

In a twenty-first aspect, the present invention provides a therapeutic method, comprising:

administering to a patient an effective amount of the peptide as described in the first aspect, the antigen-presenting cell as described in the sixth aspect, the immune effector cell as described in the eighth aspect, the targeted immune cell population as described in the tenth aspect, the conjugate as described in the eleventh aspect, the antibody as described in the twelfth aspect, the vaccine as described in the fourteenth aspect, or the pharmaceutical composition as described in the fifth aspect.

In a twenty-second aspect, the present invention provides a diagnostic method, comprising:

detecting a biological sample derived from a patient for the presence of the peptide as described in the first aspect; and determining the patient as having a tumor based on the presence of the peptide in the biological sample.

Optionally, the tumor expresses both HLA-A0201 and the peptide.

Optionally, the tumor is selected from the group consisting of lung cancer, melanoma, breast cancer, nasopharyngeal carcinoma, liver cancer, gastric cancer, esophageal cancer, colorectal cancer, pancreatic cancer, skin cancer, prostate cancer, cervical cancer, leukemia, and brain tumors.

Beneficial Effects

The tumor antigen peptide TLISSLMPI (SEQ ID NO: 2) according to the present invention is produced from tumor-specific mutation of the CACNA1H gene. It is absent in normal human tissues in which the mutation does not occur, and is present only in the tumor tissue of a patient in which the mutation occurs. Because it is only present in the tumor tissue of a patient and not in the normal tissue, it has a high specificity and causes a highly specific immune response. It can cause a specific immune response against tumors. When used as a tumor vaccine, it is safer, has few side effects and rarely causes serious immune reactions as compared to other tumor peptide vaccines, and is suitable for industrial production because of its simple structure and ease to be artificially synthesized.

The specificity between the variant forms of the peptide described above and T cells does not change due to the enhanced binding affinity to HLA-A0201. Therefore, these variant forms have the same ability to activate a specific T immune as the peptide TLISSLMPI (SEQ ID NO: 2). Thus, the peptide TLISSLMPI (SEQ ID NO: 2) or the variant forms thereof can be used as a target or a vaccine for use in the biotherapies against tumors that express both HLA-A0201 and the mutant peptide. The peptide TLISSLMPI (SEQ ID NO: 2) or the variant forms thereof can be used for the prevention and treatment of tumors by means of peptide+adjuvant, or a peptide-loaded DC vaccine, or a peptide-specific DC-CTL, a DC-CIK vaccine, etc. The tumors include a variety of cancers which express the peptide sequence, such as lung cancer, melanoma, breast cancer, nasopharyngeal carcinoma, liver cancer, gastric cancer, esophageal cancer, colorectal cancer, pancreatic cancer, skin cancer, prostate cancer, cervical cancer, leukemia, brain tumors, and the like.

Furthermore, since the peptide of the present invention is present only in tumor tissues, and the presence of the free peptide in serum can be detected by mass spectrometry, it can be used as a tumor marker for the diagnosis of a tumor.

T cells (SEQ ID NO: 2 TLISSLMPI)+T2 (SEQ ID NO: 1 TLISSLRPI)

T cells (SEQ ID NO: 2 TLISSLMPI)+T2 (SEQ ID NO: 2 TLISSLMPI)

T cells (SEQ ID NO: 3 TLISSLMPL)+T2 (SEQ ID NO: 1 TLISSLRPI)

T cells (SEQ ID NO: 3 TLISSLMPL)+T2 (SEQ ID NO: 2 TLISSLMPI)

T cells (SEQ ID NO: 4 TLISSLMPV)+T2 (SEQ ID NO: 1 TLISSLRPI)

T cells (SEQ ID NO: 4 TLISSLMPV)+T2 (SEQ ID NO: 2 TLISSLMPI)

T cells (SEQ ID NO: 5 TMISSLMPI)+T2 (SEQ ID NO: 1 TLISSLRPI)

T cells (SEQ ID NO: 5 TMISSLMPI)+T2 (SEQ ID NO: 2 TLISSLMPI)

T cells (SEQ ID NO: 6 TMISSLMPL)+T2 (SEQ ID NO: 1 TLISSLRPI)

T cells (SEQ ID NO: 6 TMISSLMPL)+T2 (SEQ ID NO: 2 TLISSLMPI)

T cells (SEQ ID NO: 7 TMISSLMPV)+T2 (SEQ ID NO: 1 TLISSLRPI)

T cells (SEQ ID NO: 7 TMISSLMPV)+T2 (SEQ ID NO: 2 TLISSLMPI).

Figure 3:
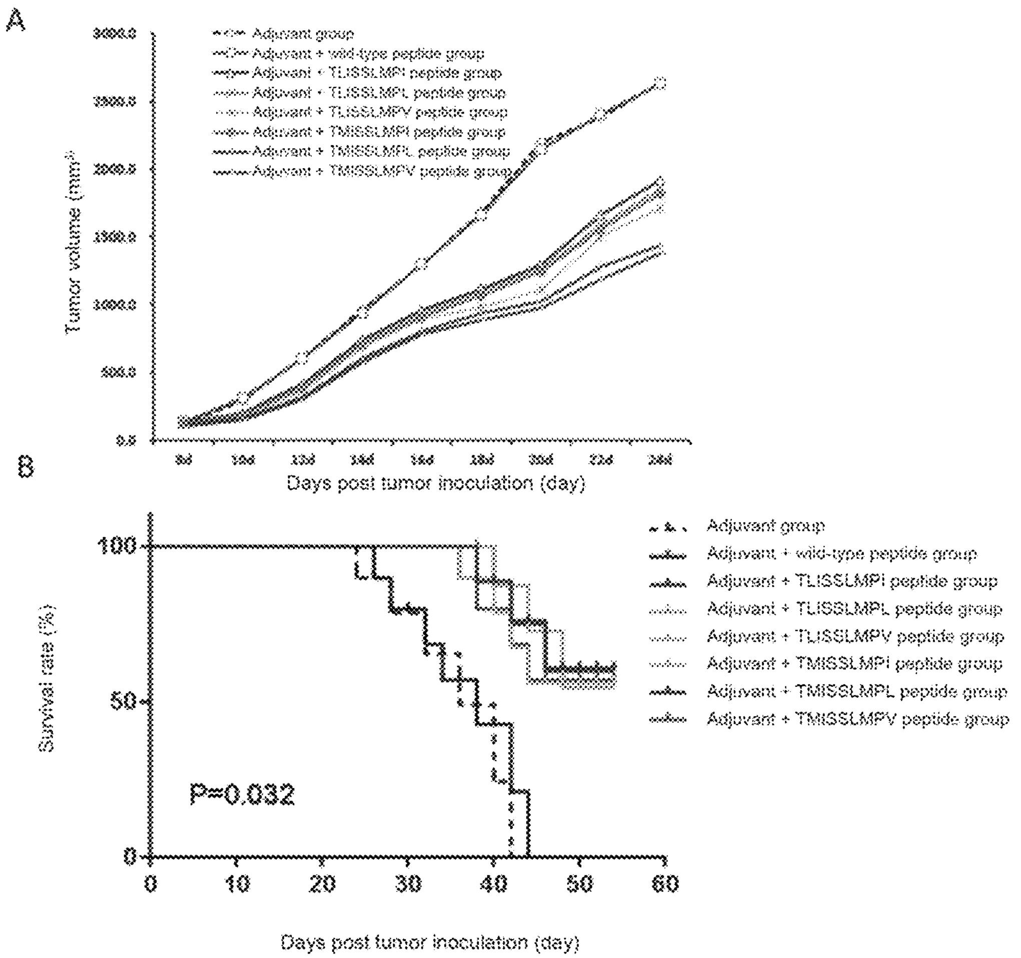

FIG. 3 shows the inhibitory effect on tumor growth and mouse survival rate after immunotherapy with the peptide of the present invention; wherein FIG. 3A shows the inhibitory effect on tumor growth after treatment with an adjuvant, an adjuvant+a wild-type peptide (TLISSLRPI, SEQ ID NO: 1), or an adjuvant+a mutant peptide TLISSLMPI (SEQ ID NO: 2) or the variant peptides thereof, FIG. 3B shows the mouse survival rate after treatment with an adjuvant, an adjuvant+a wild-type peptide, or an adjuvant+a mutant peptide TLISSLMPI (SEQ ID NO: 2) or the variant peptides thereof; wherein groups are as follows:

Adjuvant group

Adjuvant+wild-type peptide group

Adjuvant+TLISSLMPI (SEQ ID NO: 2) peptide group

Adjuvant+TLISSLMPL (SEQ ID NO: 3) peptide group

Adjuvant+TLISSLMPV (SEQ ID NO: 4) peptide group

Adjuvant+TMISSLMPI (SEQ ID NO: 5) peptide group

Adjuvant+TMISSLMPL (SEQ ID NO: 6) peptide group

Adjuvant+TMISSLMPV (SEQ ID NO: 7) peptide group.

Figure 4:
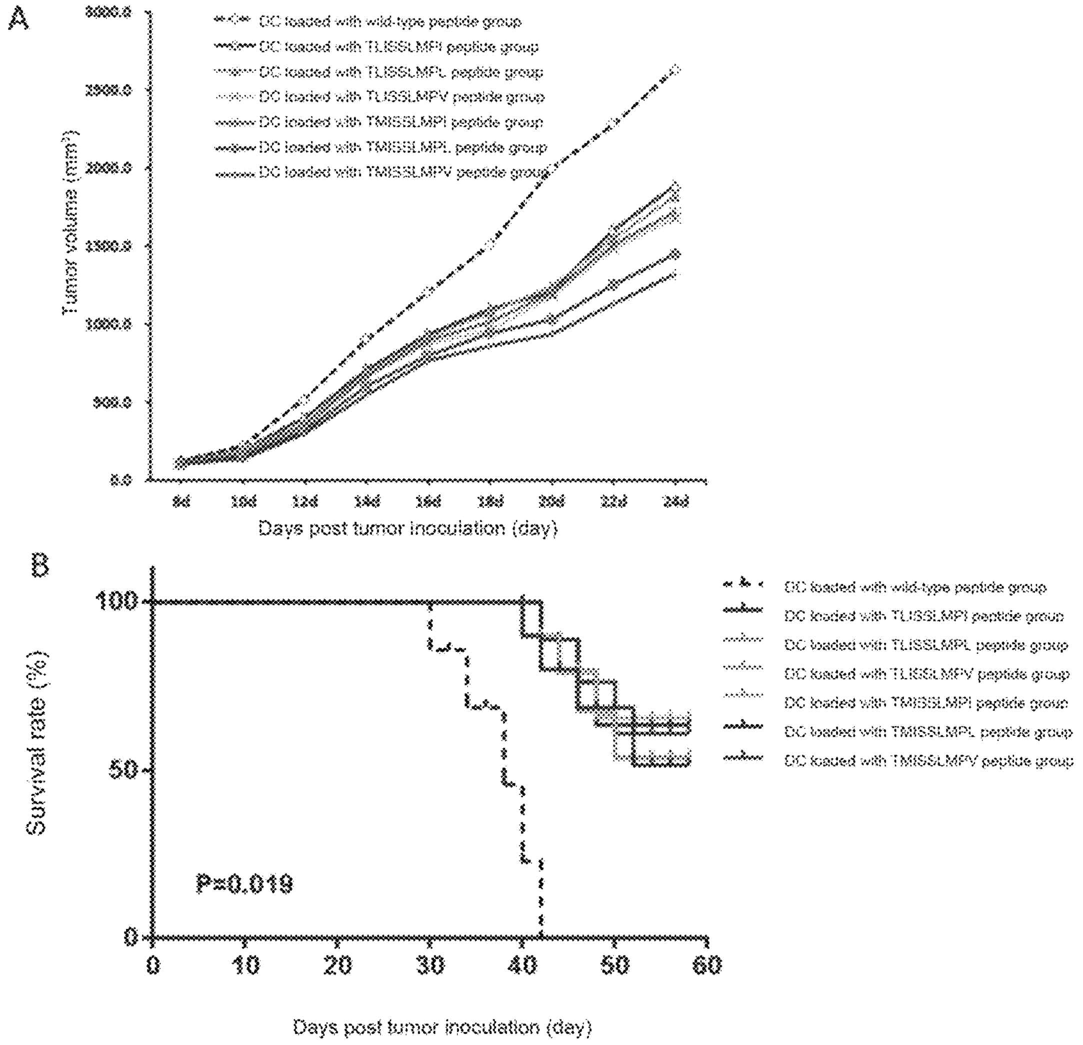

FIG. 4 shows the inhibitory effect on tumor growth and mouse survival rate after immunotherapy with the peptide of the present invention; wherein FIG. 4A shows the inhibitory effect on tumor growth after treatment with DC loaded with a wild-type peptide, or DC loaded with a mutant peptide (TLISSLMPI (SEQ ID NO: 2)) or the variant peptides thereof, FIG. 4B shows the mouse survival rate after treatment with DC loaded with a wild-type peptide, or DC loaded with a mutant peptide TLISSLMPI (SEQ ID NO: 2) or the variant peptides thereof; wherein groups are as follows:

DC loaded with wild-type peptide group

DC loaded with TLISSLMPI (SEQ ID NO: 2) peptide group

DC loaded with TLISSLMPL (SEQ ID NO: 3) peptide group

DC loaded with TLISSLMPV (SEQ ID NO: 4) peptide group

DC loaded with TMISSLMPI (SEQ ID NO: 5) peptide group

DC loaded with TMISSLMPL (SEQ ID NO: 6) peptide group

DC loaded with TMISSLMPV (SEQ ID NO: 7) peptide group.

Figure 5:
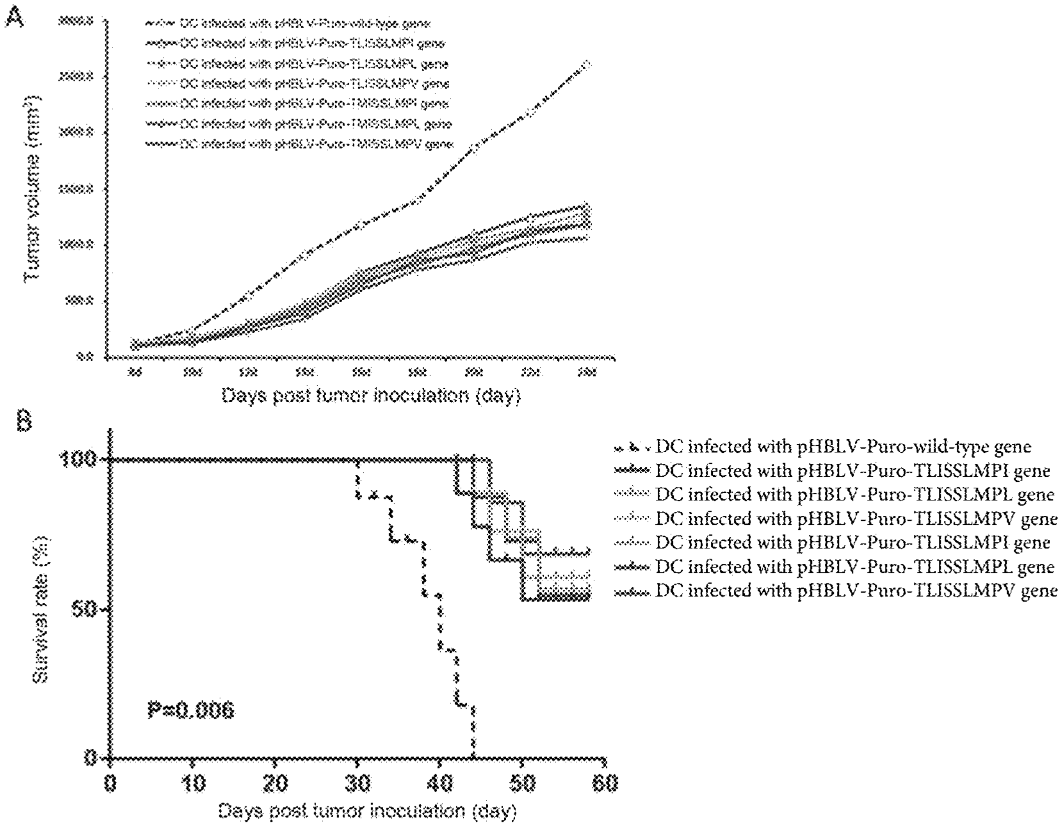

FIG. 5 shows the inhibitory effect on tumor growth and mouse survival rate after immunotherapy with the peptide of the present invention; wherein FIG. 5A shows the inhibitory effect on tumor growth after treatment with DCs infected with lentivirus vector carrying a wild-type peptide (TLISSLRPI (SEQ ID NO: 1)), or a mutant peptide (TLISSLMPI (SEQ ID NO: 2)) or the variant peptides thereof; FIG. 5B shows the mouse survival rate after treatment with DCs infected with lentivirus vector carrying a wild-type peptide (TLISSLRPI (SEQ ID NO: 1)), or a mutant peptide (TLISSLMPI (SEQ ID NO: 2)) or the variant peptides thereof; wherein groups are as follows:

DC infected with pHBLV-Puro-wild-type gene

DC infected with pHBLV-Puro-TLISSLMPI (SEQ ID NO: 2) gene

DC infected with pHBLV-Puro-TLISSLMPL (SEQ ID NO: 3) gene

DC infected with pHBLV-Puro-TLISSLMPV (SEQ ID NO: 4) gene

DC infected with pHBLV-Puro-TMISSLMPI (SEQ ID NO: 5) gene

DC infected with pHBLV-Puro-TMISSLMPL (SEQ ID NO: 6) gene

DC infected with pHBLV-Puro-TMISSLMPV (SEQ ID NO: 7) gene.

Figure 6:
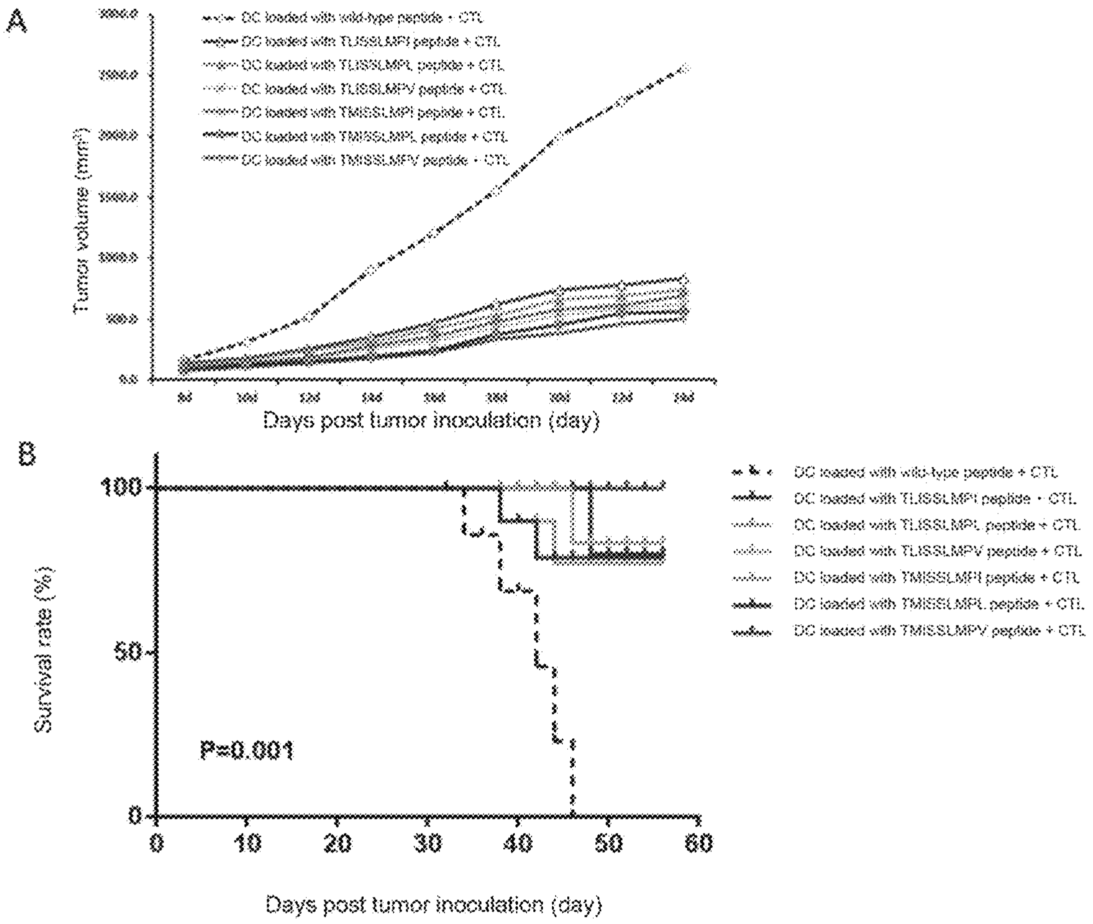

FIG. 6 shows the inhibitory effect on tumor growth and mouse survival rate after immunotherapy with the peptide of the present invention; wherein FIG. 6A shows the inhibitory effect on tumor growth after treatment with DC loaded with a wild-type peptide (TLISSLRPI (SEQ ID NO: 1))+CTL, or DC loaded with a mutant peptide (TLISSLMPI (SEQ ID NO: 2)) or the variant peptides thereof+CTL, FIG. 6B shows the mouse survival rate after treatment with DC loaded with a wild-type peptide (TLISSLRPI (SEQ ID NO: 1))+CTL, or DC loaded with a mutant peptide (TLISSLMPI (SEQ ID NO: 2)) or the variant peptides thereof+CTL; wherein groups are as follows:

DC loaded with wild-type peptide+CTL

DC loaded with TLISSLMPI (SEQ ID NO: 2) peptide+CTL

DC loaded with TLISSLMPL (SEQ ID NO: 3) peptide+CTL

DC loaded with TLISSLMPV (SEQ ID NO: 4) peptide+CTL

DC loaded with TMISSLMPI (SEQ ID NO: 5) peptide+CTL

DC loaded with TMISSLMPL (SEQ ID NO: 6) peptide+CTL

DC loaded with TMISSLMPV (SEQ ID NO: 7) peptide+CTL.

DETAILED DESCRIPTION

In order to facilitate understanding of the present invention, the following examples are exemplified in the present invention. It should be understood by those skilled in the art that the examples are only to facilitate the understanding of the present invention and should not be construed as specific limitations to the present invention.

Example 1 Affinity Prediction of the Mutant Peptides of the Present Invention Affinity of the peptides was predicted by the following procedure:

Based on the selected HLA allele type, affinity of the peptides was predicted by using a self-developed "software for predicting the binding ability of a mutant peptide based on tumor DNA and RNA sequencing" (software copyright number: 2016SR002835). The prediction results were expressed as IC50 score. An IC50 of less than 500 indicated that the peptide had an affinity, and an IC50 of less than 50 indicated that the peptide had a high affinity.

The wild-type peptide TLISSLRPI (SEQ ID NO: 1), the mutant peptide TLISSLMPI (SEQ ID NO: 2) of the present invention and the five variant peptides of the mutant peptide TLISSLMPI (SEQ ID NO: 2) (also belonging to the present invention) were obtained by standard solid phase synthesis and purified by reverse phase HPLC. The purity (>90%) and identity of the peptide were determined by HPLC and mass spectrometry, respectively. The affinity of the wild-type peptide and several mutant peptides of the present invention to HLA-A0201 was predicted by using the software for predicting the binding ability of a mutant peptide based on tumor DNA and RNA sequencing, and the prediction scores were shown in Table 1 below.

TABLE 1

Affinity prediction results of the peptides to HLA-A0201

| Mutant Peptides | IC50 (nM) | Wild-type Peptide | IC50 (nM) |
|---|---|---|---|
| TLISSLMPI (SEQ ID NO: 2) | 3.28 | TLISSLRPI | 3.39 |
| TLISSLMPL (SEQ ID NO: 3) | 3.18 | — | — |
| TLISSLMPV (SEQ ID NO: 4) | 2.86 | — | — |
| TMISSLMPI (SEQ ID NO: 5) | 2.67 | — | — |
| TMISSLMPL (SEQ ID NO: 6) | 2.49 | — | — |
| TMISSLMPV (SEQ ID NO: 7) | 2.24 | — | — |

It can be seen from Table 1 that as predicted by the computer software, the IC50 scores of the mutant peptides of the present invention were less than 50 nM, indicating that the mutant peptides of the present invention had a high affinity to HLA-A0201.

Example 2 Affinity Verification of the Mutant Peptides of the Present Invention to T2 Cells According to the manner described in Example 1, the wild-type peptide TLISSLRPI (SEQ ID NO: 1), the peptide TLISSLMPI (SEQ ID NO: 2) of the present invention and the SEQ ID NO: 2_TLISSLMPI's five variant peptides were obtained; $2\times10^5$ T2 cells (a lymphocyte, tumor cell line, expressing HLA-A0201; T2 cell is a cell strain that is deficient in an antigen peptide transporter (TAP) that is essential for endogenous antigen presentation pathway, and is a hybridoma cell from HLA-A2-positive T and B lymphocytess, and can be used to study the affinity of a peptide to HLA-A2 and the interaction of T cells with MHC-I molecule; ATCC Cat. No.: CRL-1992™) were resuspended into a 24-well plate with 500 μl of serum-free IMDM medium. 10 μg/ml of each peptide as described above was added, and human β2 microglobulin (at a final concentration of 3 μg/ml) was added and cultured overnight in an incubator (37° C., 5% $CO_2$). Two replicate wells were set up for each group. T2 cells without the addition of a peptide were used as a background control (i.e., blank), and the group added with the CMV peptide (NLVPMVATV (SEQ ID NO: 15)) was used as a positive control.

Cells were collected by centrifugation of the cell culture at 200 g for 5 minutes. The collected cells were washed twice with PBS, and then directly incubated with FITC-conjugated anti-HLA-A 0201 monoclonal antibody at 4° C. for 30 minutes. The mean fluorescence intensity (MFI) was then detected and analyzed by flow cytometer (BD FACSJazz™) and its software. The fluorescence index (FI) was calculated by using the following formula:

$$FI=[MFI_{sample}-MFI_{background}]/MFI_{background};$$

Wherein, the $MFI_{background}$ represents a value without peptide; FI>1.5 indicates that the peptide has a high affinity for HLA-A0201 molecule, 1.0<FI<1.5 indicates that the peptide has a medium affinity for HLA-A0201 molecule, and 0.5<FI<1.0 indicates that the peptide has a low affinity for HLA-A0201 molecule.

The affinity detection results of the respective peptides described above to HLA-A 0201 were shown in Table 2 below.

TABLE 2

| Affinity detection results of the peptides to HLA-A0201 | | | |
|---|---|---|---|
| Sample | Concentration of the added peptide | Average fluorescence intensity | FI |
| TLISSLRPI (SEQ ID NO: 1) | 100 μM | 672.3 | 1.99 |
| TLISSLMPI (SEQ ID NO: 2) | 100 μM | 682.7 | 2.04 |
| TLISSLMPL (SEQ ID NO: 3) | 100 μM | 692.4 | 2.08 |
| TLISSLMPV (SEQ ID NO: 4) | 100 μM | 713.6 | 2.18 |
| TMISSLMPI (SEQ ID NO: 5) | 100 μM | 701.3 | 2.12 |
| TMISSLMPL (SEQ ID NO: 6) | 100 μM | 763.9 | 2.40 |
| TMISSLMPV (SEQ ID NO: 7) | 100 μM | 776.5 | 2.46 |
| blank | 0 μM | 224.6 | 0 |
| CMV | 100 μM | 656.7 | 1.92 |

It can be seen from Table 2 that, through the affinity verification, the FI of the blank group was 0, and the FI of the CMV peptide which was used as a positive control was 1.92, both of which were normal; while the FIs of the wild-type peptide and the mutant peptides of the present invention were both greater than 1.5, further demonstrating that the wild-type peptide and the mutant peptides of the present invention were all highly affinitive.

Example 3 In Vitro Stimulation and Expansion of CD8+ T Cells by the Mutant Peptides of the Present Invention $2\times10^7$ PBMC cells were taken from the subtype HLA-A0201-positive volunteers. Mononuclear cells were isolated by an adherence method (adhering for 3 h), and CD8+ T cells were isolated by using CD8 magnetic beads. Adherent mononuclear cells were induced into immature DCs with GM-CSF (1000 U/ml) and IL-4 (1000 U/ml), and further induced into peptide-specific mature DCs with IFN-γ (100 U/ml), CD40L (100 U/ml) and each of the mutant peptide TLISSLMPI (SEQ ID NO: 2) of the present invention and the five variant peptides thereof. The mature DCs loaded with peptides were irradiated, co-cultured with CD8+ T cells from volunteers, and IL-21 was added. After 3 days, IL-2 and IL-7 were supplemented. Afterwards, IL-2 and IL-7 were again supplemented on day 5 and day 7, respectively (the final concentrations of IL-21, IL-2 and IL-7 were 30 ng/ml, 5 ng/ml and 10 ng/ml, respectively). The co-cultured cells were counted on day 10 and subsequently subjected to ELISPOTs and LDH tests. The counting results were shown in Table 3 below.

TABLE 3

| Cell counting results after culture | | |
|---|---|---|
| | Total number of cells in the well before culture | Total number of cells in the well after culture |
| TLISSLMPI (SEQ ID NO: 2) | 2.5 × 10^6 | 1.32 × 10^7 |
| TLISSLMPL (SEQ ID NO: 3) | 2.5 × 10^6 | 1.37 × 10^7 |
| TLISSLMPV (SEQ ID NO: 4) | 2.5 × 10^6 | 1.63 × 10^7 |

TABLE 3-continued

| Cell counting results after culture | | |
|---|---|---|
| | Total number of cells in the well before culture | Total number of cells in the well after culture |
| TMISSLMPI (SEQ ID NO: 5) | 2.5 × 10^6 | 1.46 × 10^7 |
| TMISSLMPL (SEQ ID NO: 6) | 2.5 × 10^6 | 1.76 × 10^7 |
| TMISSLMPV (SEQ ID NO: 7) | 2.5 × 10^6 | 1.87 × 10^7 |

It can be seen from Table 3 that after 10 days of culture, the cells proliferated significantly, and the expansion fold of the total number of cells was between 5-7 folds, indicating that the addition of the peptides of the present invention can significantly stimulate the expansion of CD8+ T cells.

Example 4 Activation of a CD8+ T Cell Immune Response by the Mutant Peptides of the Present Invention as Verified by ELISPOTs In this example, a ELISPOTs detection kit (Cat. No.: 3420-4AST-10, MABTECH) was used to verify the activation of an immune response of CD8+ T cells by the peptides of the present invention.

Principle of the ELISPOTs detection method is as follows: CD8+ T cells can specifically recognize the complex of HLA-A0201 and a peptide. The population of T cells recognizing the complex of the peptide and HLA-A0201 is varying, depending on the peptide sequence. Since T2 cells express HLA-A0201, CD8+ T cells can specifically recognize the T2 cells loaded with a peptide. After specific recognition of the complex of HLA-A0201 and the peptide, peptide-specific CD8+ T cells can be activated again to secrete IFN-γ interferon. The IFN-γ interferon secreted by the activated CD8+ T cells can be captured by antibodies on the ELISPOTs plate. Finally, the enzyme-conjugated antibody that recognizes IFN-γ can degrade the substrate through the enzyme conjugated thereto and develop color, eventually producing spots. The number of spots represents the number of cells that are activated to secrete IFN-γ interferon.

The cultured cells from Example 3 were added, along with T2 cells loaded with the mutant peptide TLISSLMPI (SEQ ID NO: 2) of the present invention and the wild-type peptide TLISSLRPI (SEQ ID NO: 1), respectively, into ELISPOTs plates, and cultured for 20 h, and then a ELISPOTs detection was performed (see the kit instruction). Finally, the spots produced by the ELISPOTs detection were counted.

The peptide was determined to have immunogenicity when the number of spots of the tested peptide/the number of spots of an unrelated peptide>2; that is, if the number of spots caused by the tested peptide is more than twice than that of an unrelated peptide, the tested peptide is determined to have immunogenicity.

ELISPOTs detection results of the respective peptides described above were shown in Table 4 below.

TABLE 4

Secretion of IFN-γ interferon by specific CD8+ T cells stimulated by a peptide

| Peptide and its variants capable of activating T cells | Number of spots in the mutant peptide group | Number of spots in the wild-type peptide group | Fold (tested/wild-type) | Conclusion |
|---|---|---|---|---|
| TLISSLMPI (SEQ ID NO: 2) | 306 | 33 | 9.27 | immunogenic |
| TLISSLMPL (SEQ ID NO: 3) | 317 | 37 | 8.57 | immunogenic |
| TLISSLMPV (SEQ ID NO: 4) | 325 | 41 | 7.93 | immunogenic |
| TMISSLMPI (SEQ ID NO: 5) | 321 | 27 | 11.88 | immunogenic |
| TMISSLMPL (SEQ ID NO: 6) | 338 | 39 | 8.67 | immunogenic |
| TMISSLMPV (SEQ ID NO: 7) | 345 | 35 | 9.86 | immunogenic |

It can be seen from Table 4 that the peptide of the present invention and its variants are immunogenic and can specifically activate a CD8+ T cell immune response.

Example 5 Specific Killing Activity of CD8+ T Cells Against Target Cells Presenting the Peptide of the Present Invention as Demonstrated by a LDH Release Assay The cells cultured in Example 3 were co-cultured with T2 cells loaded with the mutant peptides of the present invention or the wild-type peptide or without a peptide. A maximum release well, a volume correction well, a medium control well, a spontaneous release well and control wells for example at different effector-to-target ratios (ratios of T cells to T2 cells) were set in this experiment. Three replicate wells were set for each group. After 4 h, 50 μl of the co-culture supernatant was taken out and added to 50 μl of LDH substrate mixture to catalyze the reaction of LDH substrate. Finally, the plates were read at a wavelength of 490 nm, with a reference wavelength of 680 nm, and the killing activity against target cells T2 was calculated based on the control wells. The test results were shown in FIG. 2 and Table 5 below.

The formula for calculating the killing activity is:

Killing efficiency (%)=(test well−spontaneous release of effector cells−spontaneous release of target cells+medium well)/(maximum release of target cells−volume correction well−spontaneous release of target cells+medium well)×100%

TABLE 5

Specific recognition and killing of target cells presenting test peptides by T cells

| Group | effector-to-target ratio (1:1) | effector-to-target ratio (10:1) |
|---|---|---|
| T cells (SEQ ID NO: 2 TLISSLMPI) + T2 (SEQ ID NO: 1 TLISSLRPI) | 2.23% | 4.23% |
| T cells (SEQ ID NO: 2 TLISSLMPI) + T2 (SEQ ID NO: 2 TLISSLMPI) | 7.96% | 38.89% |
| T cells (SEQ ID NO: 3 TLISSLMPL) + T2 (SEQ ID NO: 1 TLISSLRPI) | 3.12% | 5.71% |
| T cells (SEQ ID NO: 3 TLISSLMPL) + T2 (SEQ ID NO: 2 TLISSLMPI) | 8.23% | 39.66% |
| T cells (SEQ ID NO: 4 TLISSLMPV) + T2 (SEQ ID NO: 1 TLISSLRPI) | 2.57% | 4.73% |
| T cells (SEQ ID NO: 4 TLISSLMPV) + T2 (SEQ ID NO: 2 TLISSLMPI) | 8.56% | 43.82% |
| T cells (SEQ ID NO: 5 TMISSLMPI) + T2 (SEQ ID NO: 1 TLISSLRPI) | 2.85% | 5.13% |
| T cells (SEQ ID NO: 5 TMISSLMPI) + T2 (SEQ ID NO: 2 TLISSLMPI) | 8.33% | 41.16% |
| T cells (SEQ ID NO: 6 TMISSLMPL) + T2 (SEQ ID NO: 1 TLISSLRPI) | 3.13% | 5.83% |
| T cells (SEQ ID NO: 6 TMISSLMPL) + T2 (SEQ ID NO: 2 TLISSLMPI) | 9.12% | 45.23% |
| T cells (SEQ ID NO: 7 TMISSLMPV) + T2 (SEQ ID NO: 1 TLISSLRPI) | 3.51% | 6.31% |
| T cells (SEQ ID NO: 7 TMISSLMPV) + T2 (SEQ ID NO: 2 TLISSLMPI) | 9.32% | 47.35% |

Figure 1:
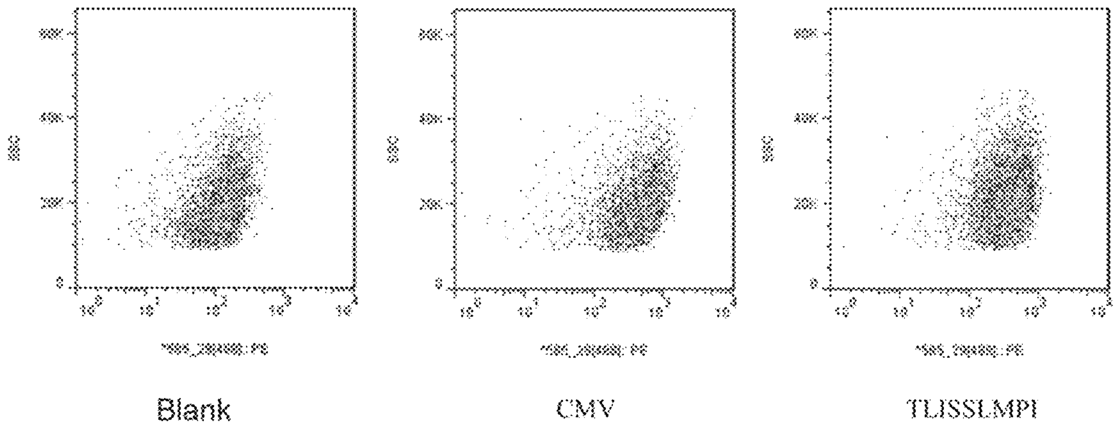
FIG. 1 is a graph showing the results of detecting the affinity of the peptide (SEQ ID NO: 2 TLISSLMPI) of the present invention to T2 cells by flow cytometry.
Figure 2:
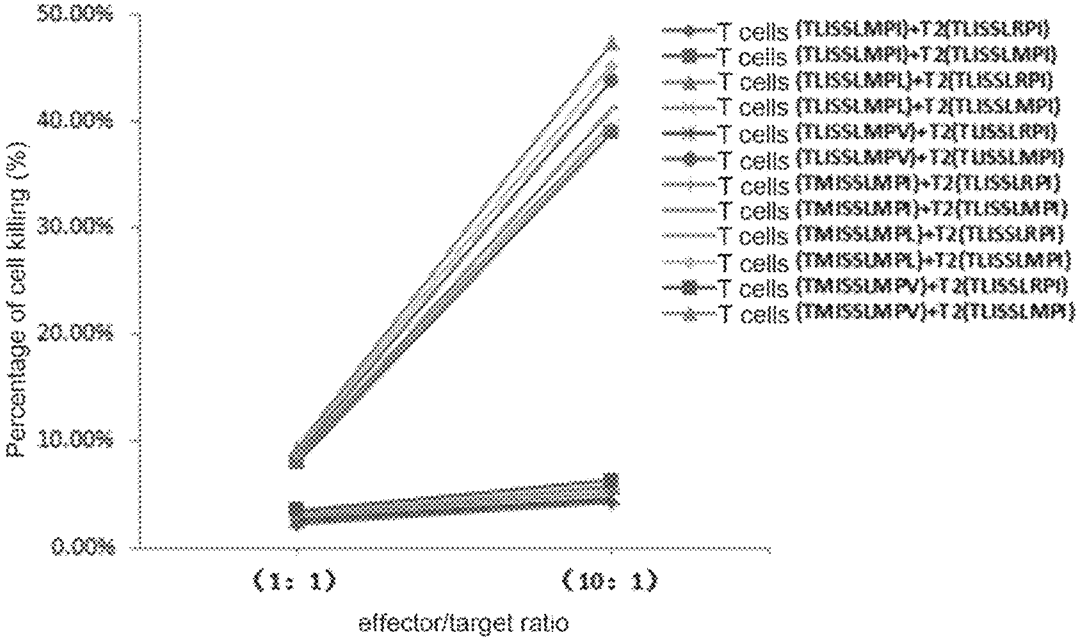
FIG. 2 is a graph showing the results of specific killing of target cells presenting the peptide of the present invention by immune cells; wherein groups are as follows.

It can be seen from the results of FIG. 2 and Table 5 that, at an effector-to-target ratio of 1:1 or 1:10, the activated T cells by the mutant peptide TLISSLMPI (SEQ ID NO: 2) of the present invention or the variant peptides thereof were capable of killing T2 cells presenting the mutant peptide, but not the T2 cells presenting a wild-type peptide, further demonstrating that the mutant peptides of the present invention were capable of specifically killing target cells presenting the mutant peptide TLISSLMPI (SEQ ID NO: 2).

Example 6 Construction and Packaging of Recombinant Lentiviruses of the Mutant Peptide TLISSLMPI (SEQ ID NO: 2) and the Variant Peptides Thereof The following DNA sequences were synthesized: "ACGCTGATATCATCACTCAGGCCCATT" (SEQ ID NO: 8), encoding the wild-type peptide TLISSLRPI (SEQ ID NO: 1); "ACGCTGATATCATCACTCATGCCCATT" (SEQ ID NO: 9), encoding the mutant peptide TLISSLMPI (SEQ ID NO: 2); "ACGCTGATATCATCACTCATGCCCCTG" (SEQ ID NO: 10), encoding the SEQ ID NO: 2 TLISSLMPI's variant peptide TLISSLMPL (SEQ ID NO: 3); "ACGCTGATATCATCACTCATGCCCGTC" (SEQ ID NO: 11), encoding the SEQ ID NO: 2 TLISSLMPI's variant peptide TLISSLMPV (SEQ ID NO: 4); "ACGATGATATCATCACTCATGCCCATT" (SEQ ID NO: 12), encoding the SEQ ID NO: 2 TLISSLMPI's variant peptide TMISSLMPI (SEQ ID NO: 5); "ACGATGATATCATCACTCATGCCCCTG" (SEQ ID NO: 13), encoding the SEQ ID NO: 2 TLISSLMPI's variant peptide TMISSLMPL (SEQ ID NO: 6); and "ACGATGATATCATCACTCATGCCCGTC" (SEQ ID NO: 14), encoding the SEQ ID NO: 2_TLISSLMPI's variant peptide TMISSLMPV (SEQ ID NO: 7). The wild-type peptide TLISSLRPI (SEQ ID NO: 1), the mutant peptide TLISSLMPI (SEQ ID NO: 2) and the mutant peptide SEQ ID NO: 2 TLISSLMPI's variant peptides were constructed into the lentiviral vector pHBLV-Puro, respectively, to name as pHBLV-Puro-TLISSLRPI (SEQ ID NO: 1), pHBLV-Puro-TLISSLMPI (SEQ ID NO: 2), pHBLV-Puro-TLISSLMPL (SEQ ID NO: 3), pHBLV-Puro-TLISSLMPV (SEQ ID NO: 4), pHBLV-Puro-TMISSLMPI (SEQ ID NO: 5), pHBLV-Puro-TMISSLMPL (SEQ ID NO: 6) and pHBLV-Puro-TMISSLMPV (SEQ ID NO: 7), respectively.

The seven lentiviral constructs were co-transfected into 293T cells with helper plasmids pSPAX2 and pMD2G for packaging, and lentiviruses of the wild-type peptide TLISSLRPI (SEQ ID NO: 1), the mutant peptide TLISSLMPI (SEQ ID NO: 2) and the mutant peptide's variant peptides were obtained.

Example 7 Establishment of a Human Lung Cancer Cell Line Expressing the Mutant Peptide TLISSLMPI (SEQ ID NO: 2

The human non-small cell lung adenocarcinoma cell line NCI-H2087 which was HLA-A*0201 positive was purchased from ATCC. The cells were cultured in DMEM medium containing 10% fetal bovine serum, 100 U/mL penicillin and 100 U/ml streptomycin in an incubator at 37° C., 5% $CO_2$. The lentivirus of TLISSLMPI (SEQ ID NO: 2) as packaged in Example 6 was transfected into the H2087 cell line. Transfected cells were continuously screened by using antibiotic puromycin to finally establish a H2087 cell line expressing TLISSLMPI (SEQ ID NO: 2) peptide which was named as H2087-TLISSLMPI (SEQ ID NO: 2) cell line.

Example 8 Human Immune Reconstitution in NOD SCID Mice 600-900 ml of anticoagulated peripheral blood was collected from healthy volunteers for isolating peripheral blood mononuclear cells (PBMCs) via Ficoll. Cells were collected for use. $2\times10^7$ PBMCs per 0.5 ml was intraperitoneally injected into each of 300 NOD SCID mice without immune leakage to perform human immune reconstitution in NOD SCID mice. After 4 weeks, the mice were selected to be inoculated with the human lung cancer cell line.

Example 9 Establishment of a Subcutaneous Xenograft Model of H2087-TLISSLMPI (SEQ ID NO: 2

The human non-small cell lung adenocarcinoma cell line H2087-TLISSLMPI (SEQ ID NO: 2) as established in Example 7 was cultured in DMEM medium containing 10% fetal bovine serum, 100 U/mL penicillin and 100 U/mL streptomycin in an incubator at 37° C., 5% $CO_2$. H2087-TLISSLMPI (SEQ ID NO: 2) tumor cells were collected, centrifuged at 1500 rpm for 5 min, and washed 3 times with sterile physiological saline. The tumor cells were diluted appropriately. To 40 μl of cell suspension was added 10 μl of 0.4% phenol blue for staining and microscopically counting cells. A tumor cell suspension at a concentration of $1*10^8$ cells/ml was prepared. 100 μl of the tumor cell suspension was inoculated subcutaneously into a NOD/SCID mouse or an immune-reconstituted NOD/SCID mouse. After inoculation, the inoculation site was daily observed for the presence or absence of an infection. It was also observed whether there was a spontaneous regression after tumor growth. The long diameter a and the short diameter b of the tumor were measured with a vernier caliper every 2-3 days and the size of the tumor was calculated as a*b*b/2. The mice and tumors were weighed and recorded every day. After 7 days, a tumor with about the size of a grain of rice could be touched under the skin of mouse. At this time, the H2087-TLISSLMPI (SEQ ID NO: 2) subcutaneous tumor model NOD/SCID mice were treated with DC-CTL vaccines. The H2087-TLISSLMPI (SEQ ID NO: 2) subcutaneous tumor model NOD/SCID mice that had been subjected to immune reconstitution for 4 weeks were treated with a peptide+complete Freund's adjuvant, or a peptide+DC vaccine, or lentivirus-infected DC vaccine, and DC-CTL vaccine, respectively. The tumor volume and the survival rate of mice were recorded every 2 days.

Example 10 Treatment Regimen with Peptide Vaccines

The H2087-TLISSLMPI (SEQ ID NO: 2) subcutaneous tumor model NOD/SCID mice that had been subjected to immune reconstitution for 4 weeks were randomly divided into 8 groups: adjuvant+wild-type peptide group, adjuvant group, adjuvant+TLISSLMPI (SEQ ID NO: 2) peptide group, and groups of adjuvant+each of the SEQ ID NO: 2 TLISSLMPI's 5 variant peptides, with 6 mice per group. The first immunization dose of the peptides described above was 100 μg/mouse. Each of the peptides was resuspended in PBS, mixed with 150 μl of Freund's complete adjuvant per mouse, and then adjusted with PBS to 300 μl per mouse, and injected subcutaneously at two points on the back. After 2 weeks, the same dose was used for booster immunization (using a complete Freund's adjuvant for the first one, and using an incomplete Freund's adjuvant for the others), with a total of 4 immunizations. The general characteristics including mental state, activity, response, diet, body weight and tumor growth of the tumor-bearing mice were observed daily. The longest diameter (a) and the shortest diameter (b) of a tumor were measured with a vernier caliper every 2 days. Tumor volume was calculated as: ½×length×width$^2$. The results were shown in FIG. 3. The results showed that, as compared to the adjuvant alone group and the wild-type peptide group, TLISSLMPI (SEQ ID NO: 2) or its variant forms+Freund's adjuvant effectively inhibited tumor growth and prolonged the survival period of mice. The formula for calculating the survival period was as follows: survival rate within a certain period of time=surviving mice within this period of time/(surviving mice within this period of time+dead mice within this period of time)*100%.

Example 11 Preparation of a DC Peptide Vaccine and Treatment Regimen Using this Vaccine 100-150 ml of anticoagulated peripheral blood was collected from healthy volunteers for isolating peripheral blood mononuclear cells via Ficoll. PBMCs were collected, resuspended in RPMI 1640 medium at $2\text{-}3\times10^6$ cells/ml, and incubated at 37° C. for 2 h. The adherent cells which were DCs were induced into mature DCs with 1000 U/ml GM-CSF, 1000 U/ml IL-4, 100 U/ml IFN-γ and 100 U/ml CD40L. Mature DCs were harvested, and then wild-type peptide, the mutant peptide TLISSLMPI (SEQ ID NO: 2) and the SEQ ID NO: 2 TLISSLMPI's five variant peptides (at a concentration of 10 μg/ml) were added respectively, co-incubated for 4 hours and then washed with physiological saline for three times. The DCs loaded with a peptide were adjusted to $(4.0\pm0.5)\times10^7$ cells/ml with physiological saline for subsequent experiments.

Tumor-bearing mice were randomly divided into 7 groups: DC loaded with wild-type peptide group, DC loaded with the mutant peptide TLISSLMPI (SEQ ID NO: 2) group, and groups of DC loaded with each of the SEQ ID NO: 2_TLISSLMPI's 5 variant peptides, with 6 mice per group. Cell suspensions of the DCs loaded with wild-type peptide, the DCs loaded with the mutant peptide TLISSLMPI (SEQ ID NO: 2), and the DCs loaded with each of the SEQ ID NO: 2 TLISSLMPI's 5 variant peptides were prepared. 0.1 ml was injected intracutaneously into each side of the inner thigh near groin of the tumor-bearing mouse once a week. For each group, the dose was $(4.0\pm0.5)\times10^6$ cells/injection, and a total of 2 injections was performed. After injection, vital signs of the mice were observed, and the vertical and horizontal dimensions of tumors were measured with a vernier caliper every two days. Tumor volume was calculated as follows: tumor volume=½×length×width$^2$. At the same time, the changes in body weight and survival of the mice were recorded. The results were shown in FIG. 4. The results in FIG. 4 showed that, compared to the group of DC vaccine loaded with wild-type peptide, DC vaccines loaded with TLISSLMPI (SEQ ID NO: 2) or the variant peptides thereof significantly prolonged survival period of mice and slowed down tumor growth in mice.

Example 12 Preparation of a DC Vaccine by Injection with Recombinant Lentivirus Containing a Peptide Gene and Treatment Regimen Using this Vaccine 100-150 ml of anticoagulated peripheral blood was collected from healthy volunteers for isolating peripheral blood mononuclear cells via Ficoll. PBMCs were collected, and incubated at 37° C. for 2 h. Non-adherent cells were washed away and DCs were cultured with recombinant human granulocyte-macrophage colony-stimulating factor (rhGM-CSF) and recombinant human interleukin-4 (rhIL-4). On day 5 of culturing, half of the medium was replaced and the cell density was adjusted to $1*10^6$ cell/ml; solutions of recombinant lentiviruses of the wild-type peptide TLISSLRPI (SEQ ID NO: 1), the mutant peptide TLISSLMPI (SEQ ID NO: 2) or the SEQ ID NO: 2_TLISSLMPI's five variant peptides (as constructed in Example 6) were added at an appropriate amount. After 24 h, the virus-containing culture medium was removed, and a culture medium containing 50 ng/ml rhIL-4, 100 ng/ml rh GM-CSF, 100 U/ml IFN-γ and 100 U/ml CD40L was added for culturing in an incubator at 37° C., 5% $CO_2$. After 16 h, the DCs were adjusted to $(4.0\pm0.5)\times10^7$ cells/ml for subsequent experiments.

Tumor-bearing mice were randomly divided into 7 groups: wild-type peptide-DC group, TLISSLMPI (SEQ ID NO: 2) peptide-DC group, and groups of each of the SEQ ID NO: 2 TLISSLMPI's 5 variant peptides-DC, with 6 mice per group. Cell suspensions of the DCs loaded with wild-type peptide, the DCs loaded with the mutant peptide TLISSLMPI (SEQ ID NO: 2), and the DCs loaded with each of the SEQ ID NO: 2 TLISSLMPI's 5 variant peptides were prepared. 0.1 ml was injected intracutaneously into each side of the inner thigh near groin of the immune-reconstituted tumor-bearing mouse once a week. For each group, the dose was $(4.0\pm0.5)\times10^6$ cells/injection, and a total of 2 injections was performed. After injection, vital signs of the mice were observed, and the vertical and horizontal dimensions of tumors were measured with a vernier caliper every two days. Tumor volume was calculated as follows: tumor volume=½×length×width$^2$. At the same time, the changes in body weight and survival of the mice were recorded. The results were shown in FIG. 5 which showed that the DC vaccines infected with recombinant lentivirus containing gene of the mutant peptide TLISSLMPI (SEQ ID NO: 2) or its five variant peptides had significant tumor-suppressing effects and prolonged the survival period of mice compared to the group of wild-type peptide which had no effect on this tumor.

Example 13 Preparation of a Peptide-Specific CTL Vaccine and a In Vivo Treatment Regimen Using this Vaccine 100-150 ml of anticoagulated peripheral blood was collected from healthy volunteers for isolating peripheral blood mononuclear cells via Ficoll. PBMCs were collected, resuspended in RPMI 1640 medium at $2\text{-}3\times10^6$ cells/ml, and incubated at 37° C. for 2 h. The non-adherent cells, which were peripheral blood lymphocytes (PBLs), were pipetted.

The collected PBLs were subjected to magnetic bead sorting to obtain CD8+ T cells, which were sensitized by co-incubation with DCs loaded with the wild-type peptide, DCs loaded with the mutant peptide TLISSLMPI (SEQ ID NO: 2) and its five variant peptides at a cell ratio of DCs:CD8+ T cells=1:4. 500 IU/ml of IL-2 and 50 ng/ml of IL-7 were added to the medium to co-incubate in an incubator at 37° C., 5% $CO_2$, and cell counting was performed after 1 week of culturing; a second round of stimulation was performed at week 2 by adding DCs loaded with TLISSLMPI (SEQ ID NO: 2) peptide, DCs loaded with the SEQ ID NO: 2_TLISSLMPI's five variant peptides, or DCs loaded with the wild-type peptide, and 500 IU/ml of IL-2. The same procedure was carried out at week 3. Thus, three rounds of stimulation were performed. Medium was appropriately added during culturing. The number of lymphocytes was counted and a cell proliferation index (PI) was calculated on days 0, 7, 14, and 21 of culture, respectively. PI=number of cells after expansion/number of cells inoculated. On day 7 after the third stimulation (i.e., day 21 of culture), cells, i.e., cytotoxic T lymphocytes (CTLs) were harvested. The cells were resuspended in physiological saline to a volume of 0.2 ml, and were reinfused through tail vein at about $1\times10^8$ cells per tumor model mouse. After injection, vital signs of the mice were carefully observed and the vertical and horizontal dimensions of the tumors were measured with a vernier caliper every 2 days.

The results were shown in FIG. 6. The results in FIG. 6 showed that, compared to the wild-type peptide group, the DC-CTL vaccines that were activated by the mutant peptide TLISSLMPI (SEQ ID NO: 2) or the five variant peptides thereof had significant tumor-suppressing effects and prolonged the survival period of mice.

The Applicant states that the method of the present invention and application and effects thereof are illustrated through the above examples, however, the present invention is not limited thereto. Those skilled in the art should understand that, for any improvement of the present invention, the equivalent replacement of the products of the present invention, the addition of auxiliary components, and the selection of specific modes, etc., will all fall within the scope of protection and the scope of disclosure of the present invention.

The invention claimed is:

1. An isolated peptide which has the amino acid sequence shown in SEQ ID NO: 3, SEQ ID NO: 4, SEQ ID NO: 5, SEQ ID NO: 6, or SEQ ID NO: 7.

2. The peptide according to claim 1, wherein the peptide can be recognized by CD8+ T cells.

3. An isolated nucleic acid encoding the peptide according to claim 1.

4. A vaccine for treating a cancer in a patient, comprising a peptide which has the amino acid sequence shown in SEQ ID NO: 2, SEQ ID NO: 3, SEQ ID NO: 4, SEQ ID NO: 5, SEQ ID NO: 6, or SEQ ID NO: 7;

wherein the vaccine further comprises an adjuvant; or the vaccine is a peptide-loaded DC vaccine, DC-CTL vaccine, or DC-CIK vaccine.

5. A method of treating a patient having a tumor, comprising:

administering to a patient an effective amount of the peptide which has the amino acid sequence shown in SEQ ID NO: 2, SEQ ID NO: 3, SEQ ID NO: 4, SEQ ID NO: 5, SEQ ID NO: 6, or SEQ ID NO: 7.

6. A diagnostic and treatment method, comprising:

detecting a biological sample from a patient for the presence of HLA-A0201 and a peptide which has the amino acid sequence shown in SEQ ID NO: 2, SEQ ID NO: 3, SEQ ID NO: 4, SEQ ID NO: 5, SEQ ID NO: 6, or SEQ ID NO: 7;

determining the patient as having a tumor expressing both HLA-A0201 and the peptide based on the presence of HLA-A0201 and the peptide in the biological sample and;

administering to the patient an effective amount of the peptide.

7. The vaccine of claim 4, wherein the cancer expresses a peptide which has the amino acid sequence shown in SEQ ID NO: 2, SEQ ID NO: 3, SEQ ID NO: 4, SEQ ID NO: 5, SEQ ID NO: 6, or SEQ ID NO: 7.

8. The vaccine according to claim 7, wherein the cancer is selected from the group consisting of lung cancer, melanoma, breast cancer, nasopharyngeal carcinoma, liver cancer, gastric cancer, esophageal cancer, colorectal cancer, pancreatic cancer, skin cancer, prostate cancer, cervical cancer, leukemia, and brain tumors.

9. The diagnostic and treatment method of claim 6, wherein the tumor is selected from the group consisting of lung cancer, melanoma, breast cancer, nasopharyngeal carcinoma, liver cancer, gastric cancer, esophageal cancer, colorectal cancer, pancreatic cancer, skin cancer, prostate cancer, cervical cancer, leukemia, and brain tumors.

* * * * *

SEQUENCE LISTING

<160> NUMBER OF SEQ ID NOS: 15

<210> SEQ ID NO 1

-continued

```
<211> LENGTH: 9
<212> TYPE: PRT
<213> ORGANISM: human

<400> SEQUENCE: 1

Thr Leu Ile Ser Ser Leu Arg Pro Ile
1               5


<210> SEQ ID NO 2
<211> LENGTH: 9
<212> TYPE: PRT
<213> ORGANISM: artificial sequence
<220> FEATURE:
<223> OTHER INFORMATION: the mutant CACNA1H peptide of the present
      application

<400> SEQUENCE: 2

Thr Leu Ile Ser Ser Leu Met Pro Ile
1               5


<210> SEQ ID NO 3
<211> LENGTH: 9
<212> TYPE: PRT
<213> ORGANISM: artificial sequence
<220> FEATURE:
<223> OTHER INFORMATION: the variant of the mutant CACNA1H peptide of
      the present application

<400> SEQUENCE: 3

Thr Leu Ile Ser Ser Leu Met Pro Leu
1               5


<210> SEQ ID NO 4
<211> LENGTH: 9
<212> TYPE: PRT
<213> ORGANISM: artificial sequence
<220> FEATURE:
<223> OTHER INFORMATION: the variant of the mutant CACNA1H peptide of
      the present application

<400> SEQUENCE: 4

Thr Leu Ile Ser Ser Leu Met Pro Val
1               5


<210> SEQ ID NO 5
<211> LENGTH: 9
<212> TYPE: PRT
<213> ORGANISM: artificial sequence
<220> FEATURE:
<223> OTHER INFORMATION: the variant of the mutant CACNA1H peptide of
      the present application

<400> SEQUENCE: 5

Thr Met Ile Ser Ser Leu Met Pro Ile
1               5


<210> SEQ ID NO 6
<211> LENGTH: 9
<212> TYPE: PRT
<213> ORGANISM: artificial sequence
<220> FEATURE:
<223> OTHER INFORMATION: the variant of the mutant CACNA1H peptide of
      the present application

<400> SEQUENCE: 6

Thr Met Ile Ser Ser Leu Met Pro Leu
1               5
```

-continued

```
<210> SEQ ID NO 7
<211> LENGTH: 9
<212> TYPE: PRT
<213> ORGANISM: artificial sequence
<220> FEATURE:
<223> OTHER INFORMATION: the variant of the mutant CACNA1H peptide of
      the present application

<400> SEQUENCE: 7

Thr Met Ile Ser Ser Leu Met Pro Val
1               5


<210> SEQ ID NO 8
<211> LENGTH: 27
<212> TYPE: DNA
<213> ORGANISM: artificial sequence
<220> FEATURE:
<223> OTHER INFORMATION: the nucleotide sequence encoding the wild-type
      CACNA1H peptide

<400> SEQUENCE: 8

acgctgatat catcactcag gcccatt                                        27


<210> SEQ ID NO 9
<211> LENGTH: 27
<212> TYPE: DNA
<213> ORGANISM: artificial sequence
<220> FEATURE:
<223> OTHER INFORMATION: the nucleotide sequence encoding the mutant
      CACNA1H peptide of the present application

<400> SEQUENCE: 9

acgctgatat catcactcat gcccatt                                        27


<210> SEQ ID NO 10
<211> LENGTH: 27
<212> TYPE: DNA
<213> ORGANISM: artificial sequence
<220> FEATURE:
<223> OTHER INFORMATION: the nucleotide sequence encoding the variant of
      the mutant CACNA1H peptide of the present application

<400> SEQUENCE: 10

acgctgatat catcactcat gcccctg                                        27


<210> SEQ ID NO 11
<211> LENGTH: 27
<212> TYPE: DNA
<213> ORGANISM: artificial sequence
<220> FEATURE:
<223> OTHER INFORMATION: the nucleotide sequence encoding the variant of
      the mutant CACNA1H peptide of the present application

<400> SEQUENCE: 11

acgctgatat catcactcat gcccgtc                                        27


<210> SEQ ID NO 12
<211> LENGTH: 27
<212> TYPE: DNA
<213> ORGANISM: artificial sequence
<220> FEATURE:
<223> OTHER INFORMATION: the nucleotide sequence encoding the variant of
      the mutant CACNA1H peptide of the present application

<400> SEQUENCE: 12

acgatgatat catcactcat gcccatt                                        27
```

-continued

```
<210> SEQ ID NO 13
<211> LENGTH: 27
<212> TYPE: DNA
<213> ORGANISM: artificial sequence
<220> FEATURE:
<223> OTHER INFORMATION: the nucleotide sequence encoding the variant of
      the mutant CACNA1H peptide of the present application

<400> SEQUENCE: 13

acgatgatat catcactcat gcccctg                                          27


<210> SEQ ID NO 14
<211> LENGTH: 27
<212> TYPE: DNA
<213> ORGANISM: artificial sequence
<220> FEATURE:
<223> OTHER INFORMATION: the nucleotide sequence encoding the variant of
      the mutant CACNA1H peptide of the present application

<400> SEQUENCE: 14

acgatgatat catcactcat gcccgtc                                          27


<210> SEQ ID NO 15
<211> LENGTH: 9
<212> TYPE: PRT
<213> ORGANISM: artificial sequence
<220> FEATURE:
<223> OTHER INFORMATION: CMV peptide

<400> SEQUENCE: 15

Asn Leu Val Pro Met Val Ala Thr Val
1               5
```